(12) United States Patent
Ivinson et al.

(10) Patent No.: US 10,730,171 B2
(45) Date of Patent: Aug. 4, 2020

(54) BASE FOR DISPOSABLE SELECTABLE TORQUE LIMITING DEVICE

(71) Applicant: ECA Medical Instruments, Newbury Park, CA (US)

(72) Inventors: David Ivinson, Camarillo, CA (US); John Nino, Simi Valley, CA (US)

(73) Assignee: ECA Medical Instruments, Newbury Park, CA (US)

( * ) Notice: Subject to any disclaimer, the term of this patent is extended or adjusted under 35 U.S.C. 154(b) by 818 days.

(21) Appl. No.: 15/203,694

(22) Filed: Jul. 6, 2016

(65) Prior Publication Data

US 2016/0311093 A1 Oct. 27, 2016

Related U.S. Application Data

(63) Continuation of application No. 14/627,877, filed on Feb. 20, 2015, now Pat. No. 9,409,285, which is a continuation of application No. PCT/US2013/040768, filed on May 13, 2013.

(60) Provisional application No. 61/694,980, filed on Aug. 30, 2012.

(51) Int. Cl.

| B25B 23/142 | (2006.01) |
|---|---|
| B25B 23/14 | (2006.01) |
| A61B 17/88 | (2006.01) |
| B25B 15/02 | (2006.01) |
| B25B 23/00 | (2006.01) |
| A61B 90/00 | (2016.01) |

(52) U.S. Cl.
CPC ...... *B25B 23/1427* (2013.01); *A61B 17/8875* (2013.01); *A61B 90/03* (2016.02); *B25B 15/02* (2013.01); *B25B 23/0042* (2013.01); *B25B 23/141* (2013.01); *B25B 23/142* (2013.01); *B25B 23/1422* (2013.01); *A61B 2090/031* (2016.02); *Y10T 29/4984* (2015.01)

(58) Field of Classification Search
CPC . B25B 23/1427; B25B 15/02; B25B 23/0042; B25B 23/141; B25B 23/14–1475; B25B 23/142; B25B 23/1422; A61B 90/03; A61B 17/8875; A61B 2090/031; Y10T 29/4984

See application file for complete search history.

(56) References Cited

U.S. PATENT DOCUMENTS

| 2,732,746 | A | * | 1/1956 | Livermont .......... B25B 23/1427 464/36 |
|---|---|---|---|---|
| 3,003,378 | A | | 10/1961 | Fred |
| 3,068,667 | A | | 12/1962 | Ernst |
| 3,168,944 | A | | 2/1965 | Zimmerman |
| 3,613,751 | A | | 10/1971 | Juhasz |
| 3,695,059 | A | | 10/1972 | Laubach |
| 3,702,546 | A | | 11/1972 | Schnepel |

(Continued)

FOREIGN PATENT DOCUMENTS

WO    WO 2005/077603 A1    8/2005

*Primary Examiner* — Bryan R Muller
(74) *Attorney, Agent, or Firm* — Ferguson Case Orr Paterson (57) ABSTRACT

A unitary base for a torque limiting device is disclosed. The base accepting a plurality of swappable torque limiting fixtures (STLF), whereby a single unitary disposable plastic base may be utilized to form a variety of different specific torque limiting devices and a method to construct and configure such a device.

12 Claims, 7 Drawing Sheets

(56) References Cited

U.S. PATENT DOCUMENTS

| | | | |
|---|---|---|---|
| 4,272,973 A | 6/1981 | Fu-Tsai | |
| 5,746,298 A | 5/1998 | Krivec et al. | |
| 5,782,831 A * | 7/1998 | Sherman | A61B 17/7079 606/103 |
| 6,132,435 A | 10/2000 | Young | |
| 6,640,674 B1 | 11/2003 | Rinner et al. | |
| 7,032,476 B2 * | 4/2006 | Lin | B25B 15/001 81/473 |
| 7,243,581 B1 * | 7/2007 | Gao | B25B 23/141 192/38 |
| 7,272,998 B1 | 9/2007 | Gauthier | |
| 7,275,467 B1 * | 10/2007 | Lee | B25B 23/1427 81/467 |
| 7,334,509 B1 | 2/2008 | Gao | |
| 7,762,164 B2 * | 7/2010 | Nino | B25B 15/02 81/475 |
| 8,105,328 B2 * | 1/2012 | Protopsaltis | A61B 17/7091 606/104 |
| 8,206,394 B2 * | 6/2012 | Stad | A61B 17/7091 606/86 A |
| 8,221,431 B2 * | 7/2012 | Chenaux | A61B 17/8875 606/916 |
| 8,276,487 B2 | 10/2012 | Wengreen et al. | |
| 2006/0016300 A1 | 1/2006 | Bubel | |
| 2006/0074418 A1 * | 4/2006 | Jackson | A61B 17/7086 606/914 |
| 2007/0213714 A1 * | 9/2007 | Justis | A61B 17/7002 606/86 A |
| 2009/0088764 A1 * | 4/2009 | Stad | A61B 17/7086 606/90 |
| 2010/0274230 A1 * | 10/2010 | Edgell | A61N 1/3752 606/1 |
| 2010/0307299 A1 | 12/2010 | Nino et al. | |
| 2011/0184425 A1 | 7/2011 | Cheraux | |
| 2013/0226192 A1 | 8/2013 | Nino et al. | |
| 2014/0224085 A1 * | 8/2014 | Merrick | B25B 13/54 81/443 |
| 2015/0202018 A1 | 7/2015 | Schaller et al. | |

* cited by examiner

FIG. 9E

BASE FOR DISPOSABLE SELECTABLE TORQUE LIMITING DEVICE

RELATED APPLICATIONS

This patent application is a Continuation of U.S. patent application Ser. No. 14/627,877 filed Feb. 20, 2015, which is a Continuation of International patent application PCT/US2013/040768, filed May 13, 2013, which claims the full Paris Convention priority to, and benefit of, U.S. provisional application No. 61/694,980, filed on Aug. 30, 2012, the contents of which are incorporated by this reference, as if fully set forth herein, in their entirety.

BACKGROUND

1. Field

This disclosure relates to a medical use driver tool and, in particular, to a torque-limiting driver base with selectable fixed torque modules, which driver disengages at a predefined torque limit.

2. General Background

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error, and these drivers must impart a precise amount of torque.

Reusable drivers require constant recalibration to ensure that the driver is imparting the precise amount of torque. Recalibration is a cumbersome task, but must be done routinely.

Disposable drivers are an easy to use and reliable alternative to the reusable drivers. Typically, each implant, for example, is packaged with a disposable driver designed to the implant's specifications. Once the driver has been used, it can be discarded. Thus, a surgeon can have complete confidence that the disposable driver, packaged with an implant, will impart the precise amount of torque.

DESCRIPTION

Torque is a measure of how much force acting on an object causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N m). The joule, which is the SI unit for energy or work, is also defined as an N m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch pounds.

A low cost, limited use, torque limiting driver will provide a series of torque limited tightening.

In some exemplary implementations aspects of a torque limiting device having a hollow body with and open proximal end and open distal end forming a handle; an internal wall bisecting said hollow body into a first and a second section; a channel formed through said internal wall fluidly connecting said first and said second sections; a nose supported on a circular base which fits movably into said hollow body; a front side of said nose with a tool extending therefrom; a backside with said nose having gears, an extended neck and a pin mounting guide and a bearing surface; a clutch having gears on its top, a pass through channel therein, an annular wall surrounding the gear, a bearing surface surrounding the gear, and a drive catch formed in the annular wall; a swappable torque limiting fixture (STLF) having an elongated body with a pin at one end and a flange with bearing at the other end; a drive spline extending from the internal wall of the hollow body and aligned with the drive catch; and, wherein the torque limiting device is formed by affixing the swappable torque limiting fixture and coil spring to the pin mounting guide via the pass through channel are disclosed. In some instances a circular cap fitted into the distal end of the body.

In some exemplary implementations, aspects of a torque limiting device having a hollow body with and open proximal end and open distal end forming a handle; an internal wall bisecting said hollow body into a first and a second section; a channel formed through said internal wall fluidly connecting said first and said second sections; a nose supported on a circular base which fits movably into said hollow body; a front side of said nose with a tool extending therefrom; a backside with said nose having gears, an extended neck and a pin mounting guide and a bearing surface with a visual identifier on the back surface; a clutch having gears on its top, a pass through channel therein, an annular wall surrounding the gear, a bearing surface surrounding the gear, and a drive catch formed in the annular wall; a swappable torque limiting fixture (STLF) having an elongated body with a pin at one end and a flange with bearing at the other end; a drive spline extending from the internal wall of the hollow body and aligned with the drive catch; and, wherein the torque limiting device is formed by affixing the swappable torque limiting fixture and coil spring to the pin mounting guide via the pass through channel are disclosed.

In some exemplary implementations, there is disclosed aspects of a torque limiting device having a hollow body with an open proximal end and open distal end forming a handle; an internal wall bisecting said hollow body into a first and a second section; a channel formed through said internal wall fluidly connecting said first and said second sections; a nose supported on a circular base which fits movably into said hollow body; a front side of said nose with a tool extending therefrom; a backside with said nose having gears, an extended neck and a pin mounting guide and a bearing surface with a visual identifier on the back surface; a clutch having gears on its top, a pass through channel therein, an annular wall surrounding the gear, a bearing surface surrounding the gear, and a drive catch formed in the annular wall; a swappable torque limiting fixture (STLF) having an elongated body with a pin at one end and a flange with bearing at the other end; a drive spline extending from the internal wall of the hollow body and aligned with the drive catch; and, wherein the torque limiting device is formed by affixing the swappable torque limiting fixture and coil spring to the pin mounting guide via the pass through channel and a circular cap is fitted into the distal end of the body with a window through the back of the cap are disclosed.

In some exemplary implementations, there are disclosed aspects of a method of selecting a specific torque limiting stroke setting for a torque limiting device, the method comprising: having a unitary base. The unitary base may include a hollow handle with a bisecting wall in fluid communication with a front and a back section of the handle formed thereby; having a drive spline extended on the interior of the back section wall for imparting force at a predetermined torque limit to a clutch; placing a movable unitary nose with a tool on its top and a mounting guide and gear its backside into the front section of the base; placing a unitary clutch with a pass through channel and a gear that mates with the nose gear inside the back section with the gear against the nose gear; selecting one of two or more swappable torque limiting fixtures (STLF), each of which has a predetermined torque rating, a mounting pin and a bearing flange; placing a coil spring around the torque limiting fixture and against the bearing flange; and, passing the pin through the pass through channel and affixing it into the mounting guide whereby the device has a fixed torque limit which is different than the torque limit would have been had another STLF been selected.

In some exemplary implementations, there is disclosed aspects of a method of selecting a specific torque limiting stroke setting for a torque limiting device, the method comprising: having a unitary hollow handle base with a bisecting wall in fluid communication with a front and a back section formed thereby; having a drive spline extended on the interior of the back section wall for imparting force at a predetermined torque limit to a clutch; placing a movable unitary nose with a tool on its top and a mounting guide and gear its backside into the front section of the base; placing a unitary clutch with a pass through channel and a gear that mates with the nose gear inside the back section with the gear against the nose gear; selecting one of two or more swappable torque limiting fixtures (STLF), each of which has a predetermined torque rating, a mounting pin and a bearing flange, with an identifier on the backside of the bearing flange; placing a coil spring around the torque limiting fixture and against the bearing flange; a end cap with a window that aligns with the identifier and, passing the pin through the pass through channel and affixing it into the mounting guide whereby the device has a fixed torque limit which is different than the torque limit would have been had another STLF been selected.

In some exemplary implementations, there is disclosed aspects of a kit for forming a torque limiting device comprising: a selection of a plurality of STLFs; a coil spring; a partially assembled torque limiting device with a movable nose on one side of a bisecting wall in a hollow body and connected movably to a clutch, via gears, on the other side of the bisecting wall; a mounting guide whereby the pin at one end of a STLF may be mounted into a guide on the backside of the nose; and, a drive spline which aligns with a drive catch on the annular wall of the clutch.

In some exemplary implementations, there is disclosed aspects of a kit for forming a torque limiting device comprising: a partially assembled torque limiting device comprising; a hollow body with and open proximal end and open distal end forming a handle; an internal wall bisecting said hollow body into a first and a second section; a channel formed through said internal wall fluidly connecting said first and said second sections; a nose supported on a circular base which fits movably into said hollow body; a front side of said nose with a tool extending therefrom; a backside with said nose having gears, an extended neck and a pin mounting guide and a bearing surface; a clutch having gears on its top, a pass through channel therein, an annular wall surrounding the gear, a bearing surface surrounding the gear, and a drive catch formed in the annular wall; a selection of swappable torque limiting fixture (STLF) each having an elongated body with a pin at one end, a flange with bearing at the other end and an identifier on the STLF providing a visual cue corresponding to the torque properties of the device if it uses that particular STLF; a drive spline extending from the internal wall of the hollow body and aligned with the drive catch; and, wherein the torque limiting device is formed by affixing the selected swappable torque limiting fixture and coil spring to the pin mounting guide via the pass through channel.

DRAWINGS

The above-mentioned features of the present disclosure will become more apparent with reference to the following description taken in conjunction with the accompanying drawings wherein like reference numerals denote like elements and in which.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures are hereby incorporated by this reference as if fully set forth herein.

FURTHER DESCRIPTION

Figure 1A:
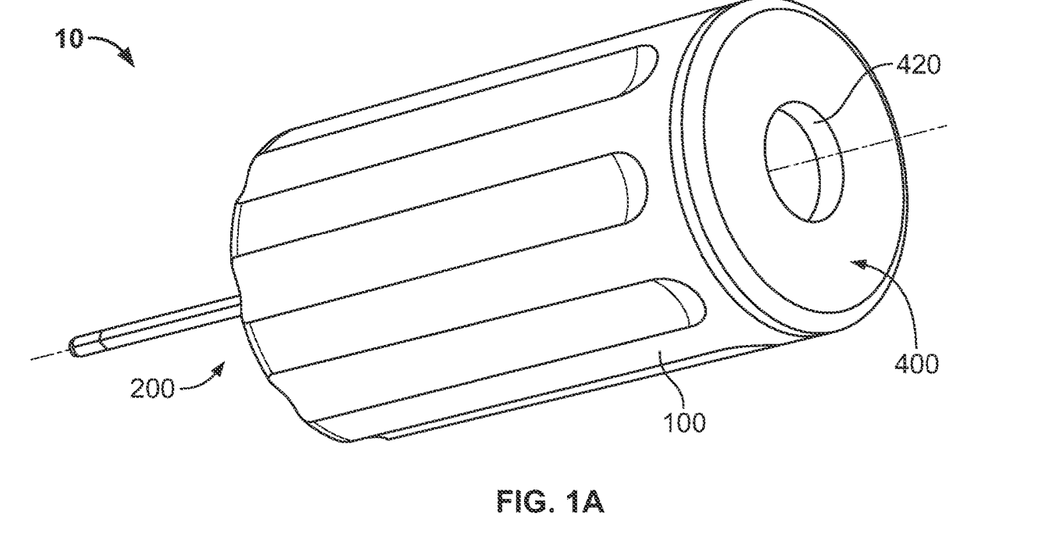
FIGS. 1A and 1B show an external overview of exemplary implementations of a torque limiting device.
Figure 1B:
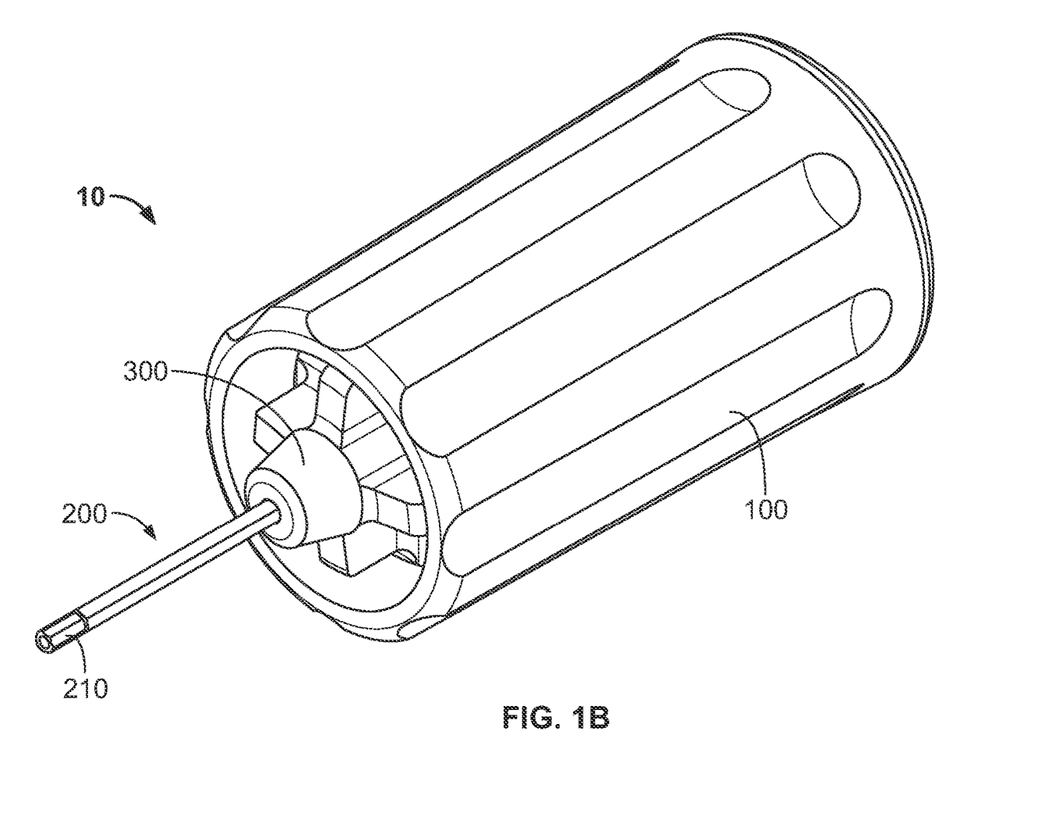
Figure 2:
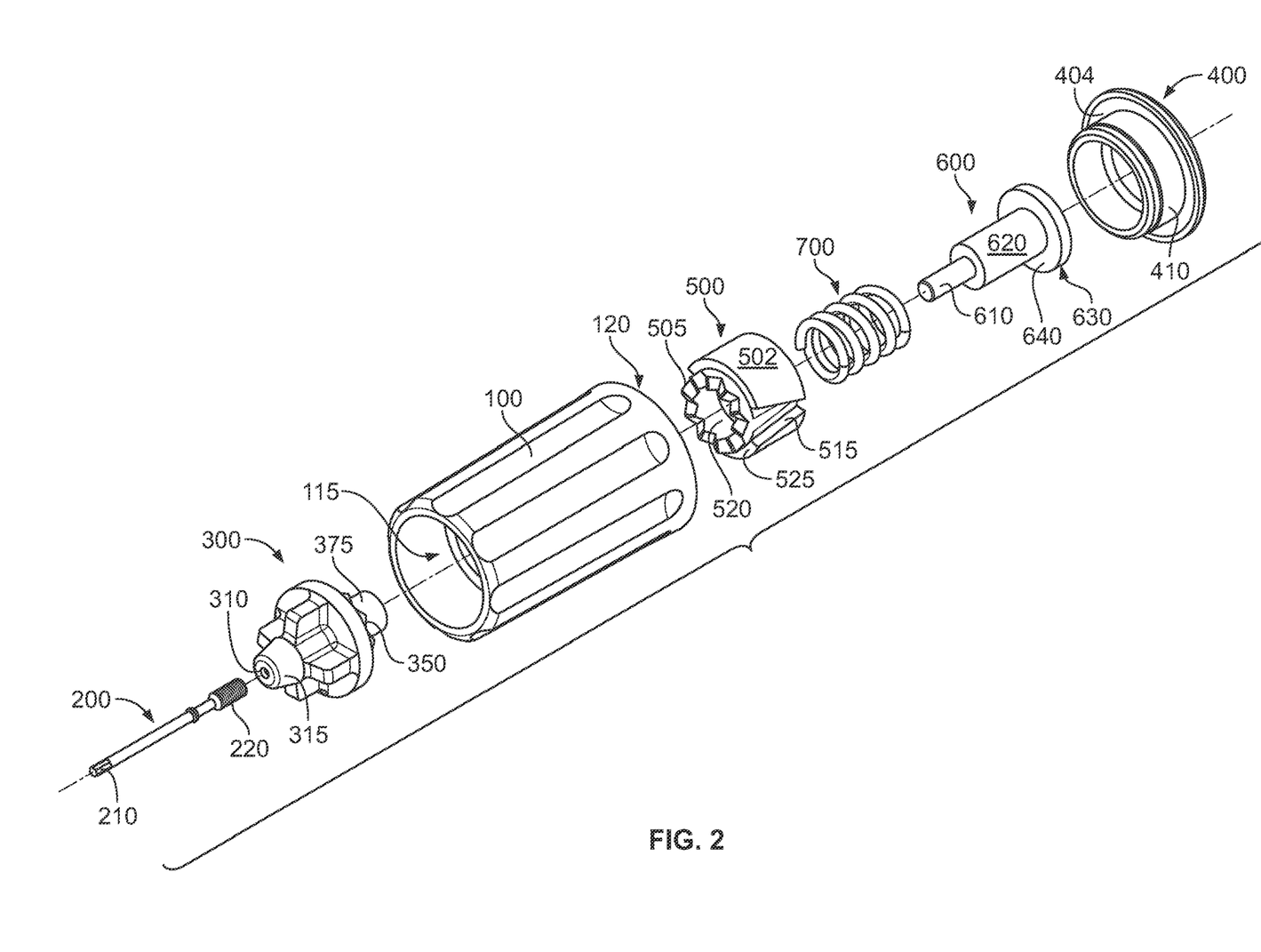
FIG. 2 shows a front to rear assembly view of some aspects of an exemplary implementation of a torque limiting device.
Figure 3:
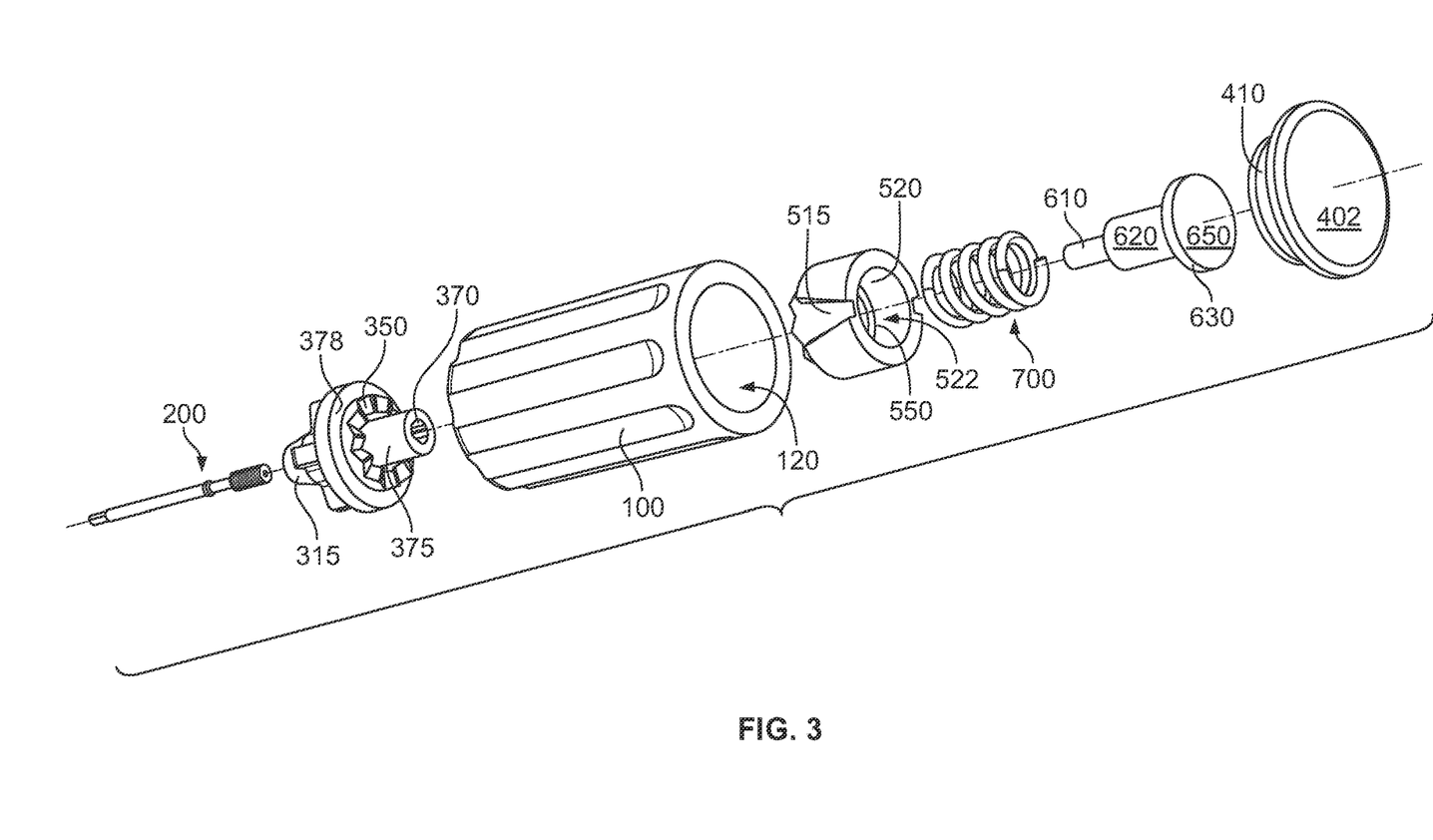
FIG. 3 shows a rear to front assembly view of some aspects of an exemplary implementation of a torque limiting device.

Referring to FIGS. 1A-1B there is disclosed a torque limiting driver 10 having a plastic molded body 100 which also may function as a handle and a tool 200 with a tip 210 on one end, said tool being fitted into a movable nose 300.

In FIGS. 2-6, there are shown various aspects, use and assembly views of exemplary implementations of torque-limiting drivers. The torque-limiting driver's molded body 100 is generally hollow with an open proximal end 115, an open distal end 120, and an internal circular wall 130 bisecting the handle into a front section 135 and a back section 145. There is fluid communication between the front and back section via centered channel 150.

A circular cap 400 with a backside 402, a front side 404, and an annular wall 410 which extends from said front side of a size and shape to form a latch with said open distal end 120. Optionally a window 420 may be formed in our through said circular cap 400 to allow a view to internal structures.

The tool 200 with tip 210 at its distal end has a fixed mount 220 at its distal end and is affixed into a mounting guide 310 located in the front 315 of the movable nose 300. The tip 210 may be a drive for mounting instruments, an instrument which is used for tightening fasteners, or a cutting instrument. To effectively apply torque via the tip, the tip must be engaged. In some instances, said engagement will be with a fastener. In other instances, said engagement may be with material to be cut or resected.

The circular nose 300, is formed with a diameter fits within said open proximal end 115. On the backside of the movable circular nose is a first gear 350 with gear teeth 351 and a pin mounting catch 370. The gear has a diameter which allows it to pass through the centered channel 150. A bearing shoulder is formed around the gear 350 which rests on said circular wall 130.

A clutch 500 including a second gear 501 is inserted into the distal end 120 fitting within the back section 145. The clutch has an annular outer wall 502, gear teeth 505 at top end which mate with the gear 350 on the movable nose 300. The clutch also has a drive-catch 515 formed in the annular wall 502 and a pass through channel 520 which in conjunction with the annular wall forms a cup shaped internal cavity 522. The drive-catch mates with a drive spline 160 on the handle 100.

Figure 4:
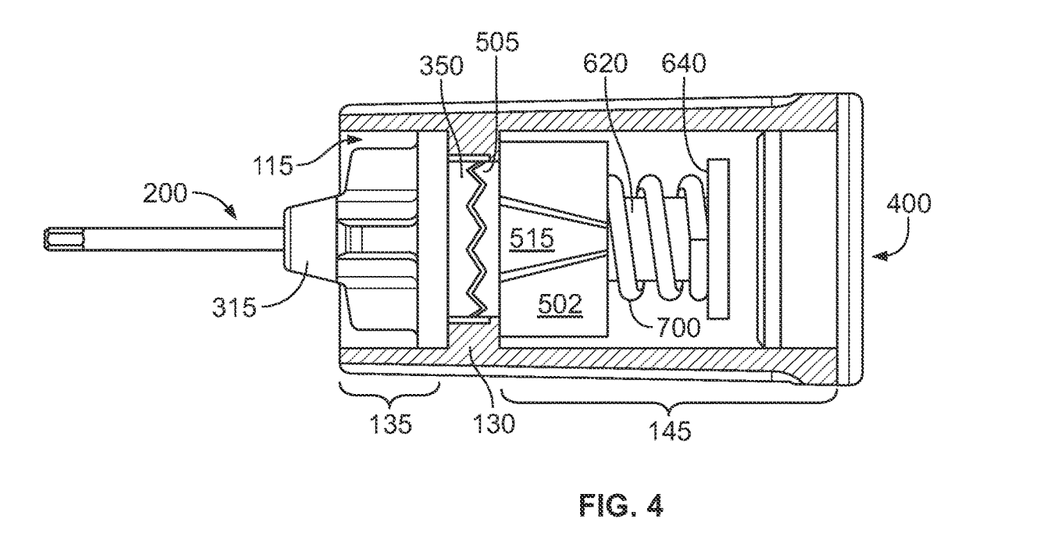
FIG. 4 shows an assembled torque limiting device with a partially cut-away handle.
Figure 5:
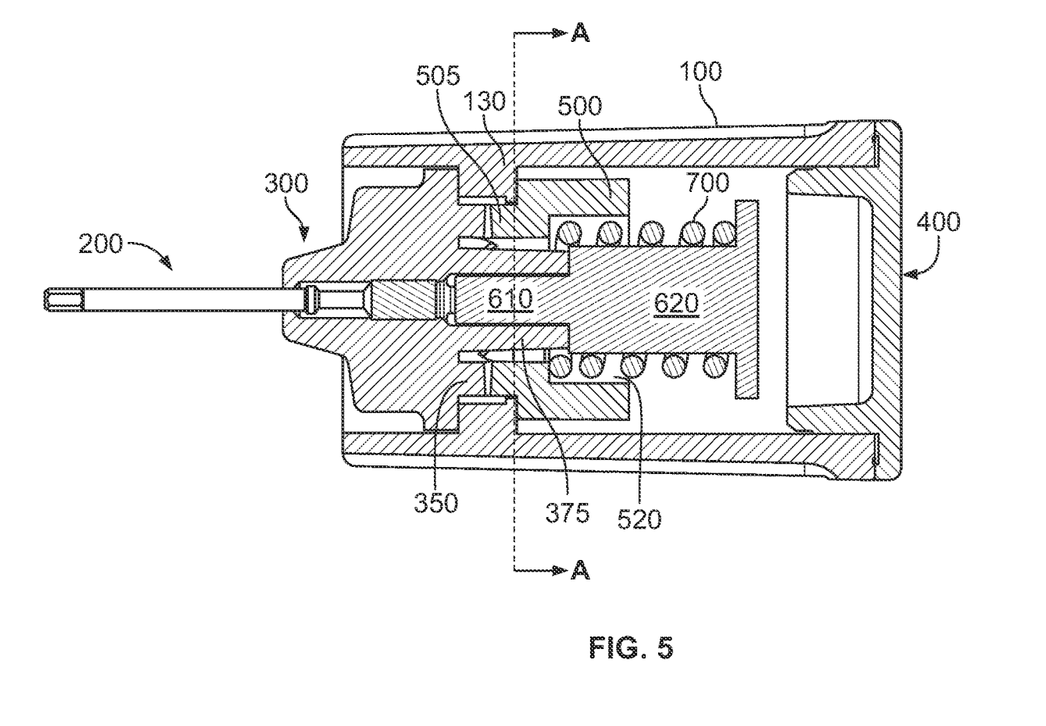
FIG. 5 shows a cut-away view of an assembled torque limiting device.
Figure 6:
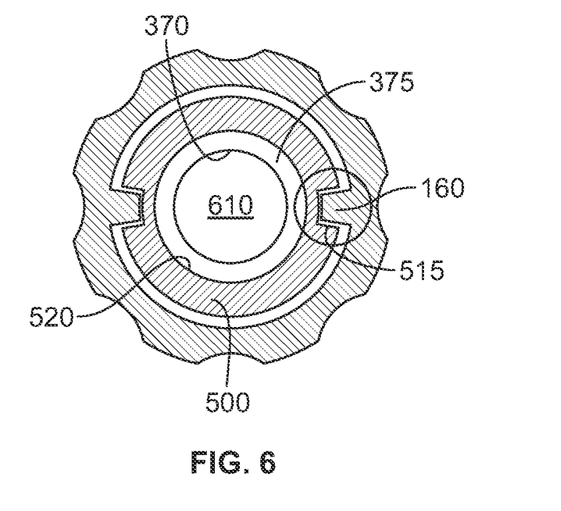
FIG. 6 shows a drive mechanism in a torque limiting device.

FIG. 6 is a cut-away sectional view of FIG. 4 along the line of "A-A" the pin 610 fitted within the mounting catch 370 which is within the pass through channel 520 of the clutch 500. The drive catch 515 of the clutch is shown with the drive spline 160 extended from the interior annular wall of the back section 145.

Via pass-through channel 520 the swappable torque limiting fixture (STLF) 600 which sets a predetermined torque for the device is inserted. Prior to insertion a coil spring 700 is placed on the STLF 600. The STLF is further comprised of a mounting pin 610 at a distal end, a body 620 contiguous with the pin and a extended flange 630. The flange has a bearing surface 640 on one side and a head surface 650 opposite the bearing surface. The coil spring 700 rests at a first end against the bearing surface 640 and at the other end against a channel bearing 550 within the cup shaped internal cavity 522 fluidly connected to the pass through channel 520. The pin 610 mates with a mounting guide 370 on an extended neck 375 formed on the backside of the movable circular nose 300. Once inserted firmly, the pin is completely encased in the mounting guide. The spring 700 is compressed a fixed amount determined by the length of the body 620. During assembly and/or to set a specific torque limit, a STLF is selected with a body 620 and a coil spring 700 which in combination set a selected torque limit.

During assembly of a torque limiting driver a device utilizing primarily the same components and with the same form factor may be set to a predetermined torque limit via selecting and assembling (or replacing) a particular STLF. The primary components consisting of at least the handle (molded body), movable nose and clutch, also referred to as a unitary based. In some instances, the end cap may be part of the unitary base. In some instances, the coil spring may be part of the unitary base. Springs may also be swapped to further alter or fine tune the torque range. In some instance a selection of STLF and/or springs may be packed together for onsite or on demand assembly to obtain the selected torque in the disposable device.

The pin 610 may be formed of a plastic or other material which is more malleable (or deformable) than the mounting guide 370, thereby causing the inserted pin 610 to deform to fit into the mounting guide. In some instances, the mounting guide is softer than the pin and deforms to accommodate the pin.

Figure 7A:
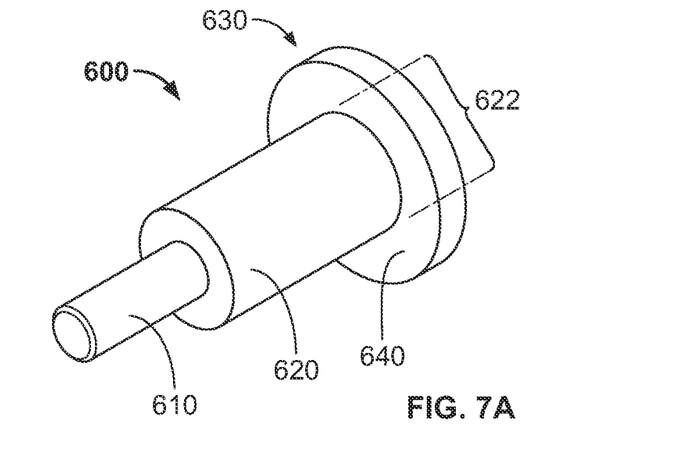
FIGS. 7A and 7B show the modular torque setting button.
Figure 7B:
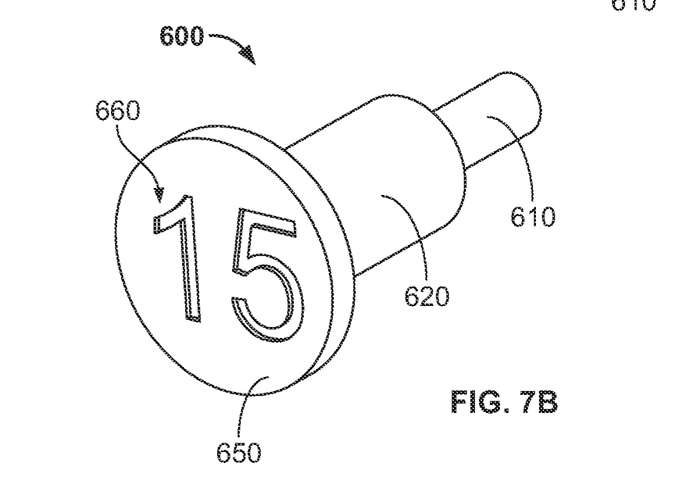

The swappable torque limiting fixture (STLF) 600 depicted in FIGS. 7A and 7B may be varied in body 620 length. Changing the body length will alter the compression and/or limits placed on the coil spring (shown in FIGS. 1-6 and 8) at the boundaries (bearing surfaces) wherein swapping a STLF with a longer body for one with a shorter body will decrease force requirements of a torque limiting driver utilizing the above exemplary implementations. The STLF has a pin 610 for mounting or catching the STLF into an object with an additional bearing surface. The body 620 is of selectable length. The flange 630 extends radially around the bottom edge 622 of the body. On the back side of the flange is the rear surface 650. An identifier 660 may be formed or placed on that back surface. Identifiers may include numbers, colors, letters, symbols or other visual designators which may be used to indicate the properties of the STLF and/or the torque limits it would impart to a device 10 it was used in.

Figure 8:
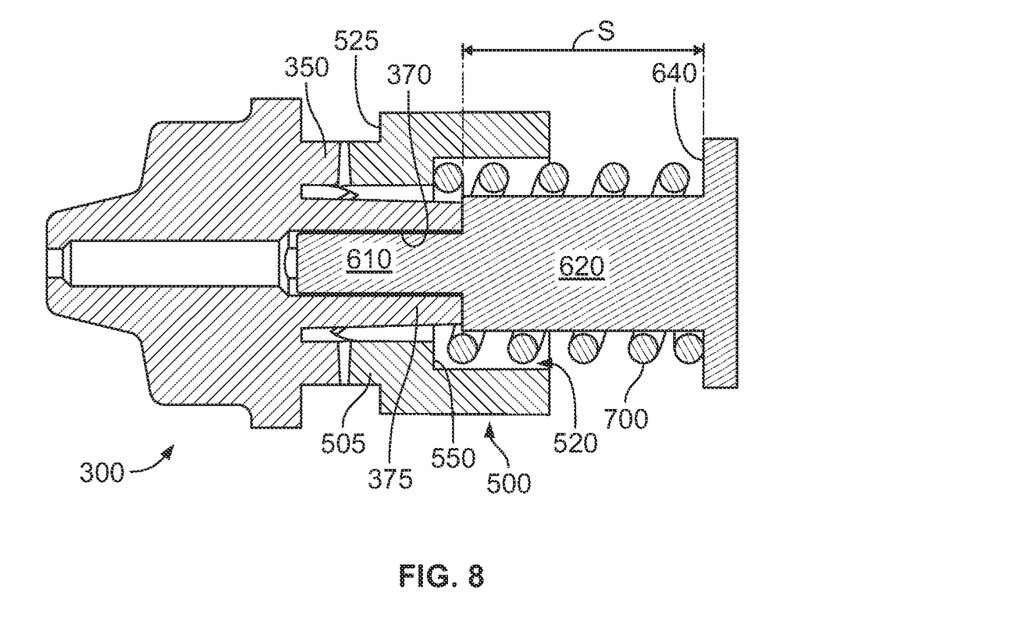
FIG. 8 shows a cut away component view of the modular button and nose spring assembly.

FIG. 8 shows a component view of the clutch 500 engaged with the nose 300 via the STLF with the pin 610 affixed within the mounting guide 370 and having coil spring 700 compressed between bearing surfaces. The bearing surface 640 on the flange 630 and bearing surface 550 along the annular wall forming the pass through channel 520 form boundaries for the coil spring. The selection of the body 620 length and/or the compression properties of the coil spring will adjust the torque limits of this device. Within functional limits, a longer body 620 (with a fixed properties spring) will result in less force requirements. A shorter body 620 will result in greater force requirements.

FIGS. 9A-9E show five variations on latch and catch configurations of mating the STLF pin into a mounting guide of the nose. These do not represent all potential configurations but those of ordinary skill in the art will recognize that variations on these mounting configurations are within the scope of this disclosure.

Figure 9A:
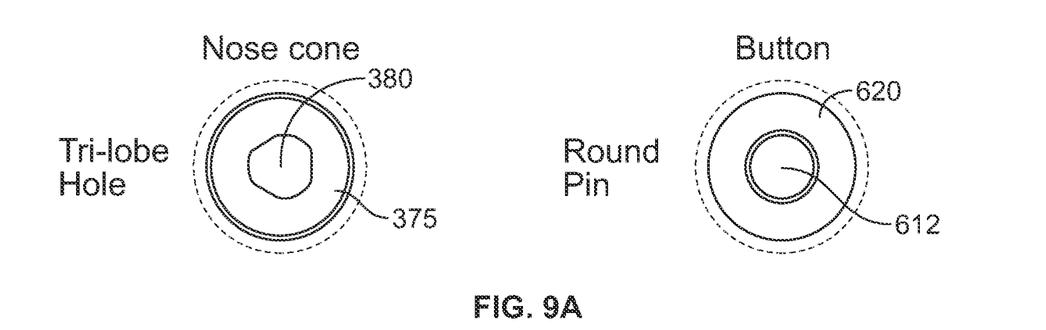
FIGS. 9A-9E show pin and nose configurations.
Figure 9B:
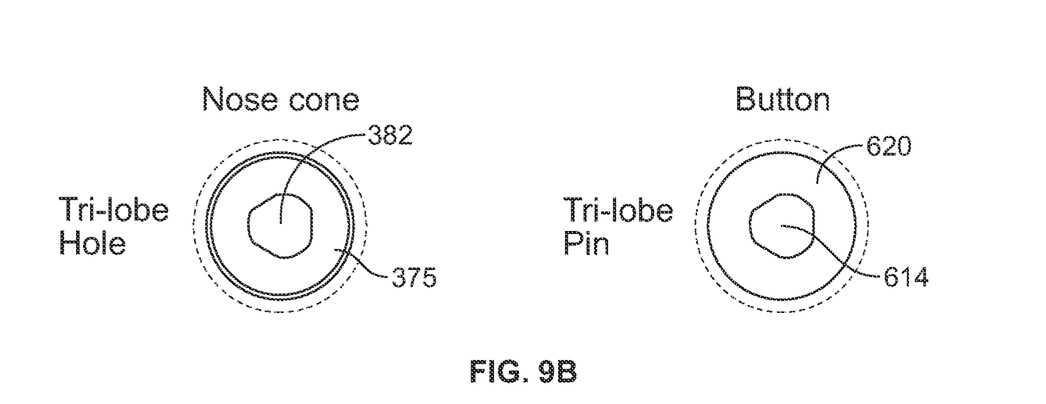
Figure 9C:
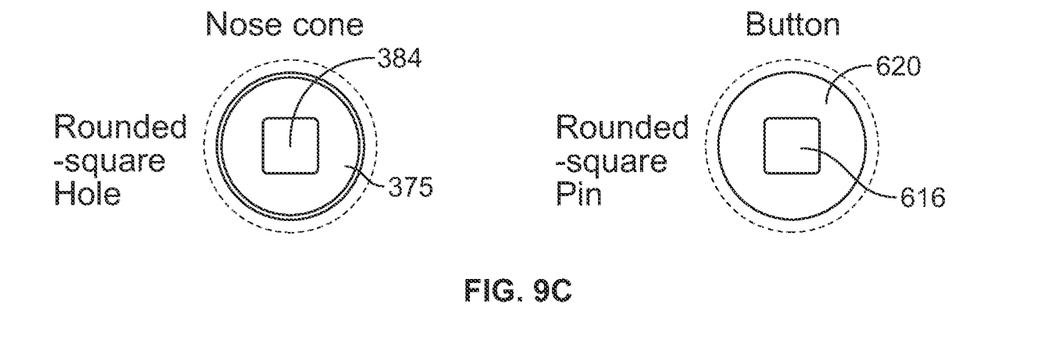
Figure 9D:
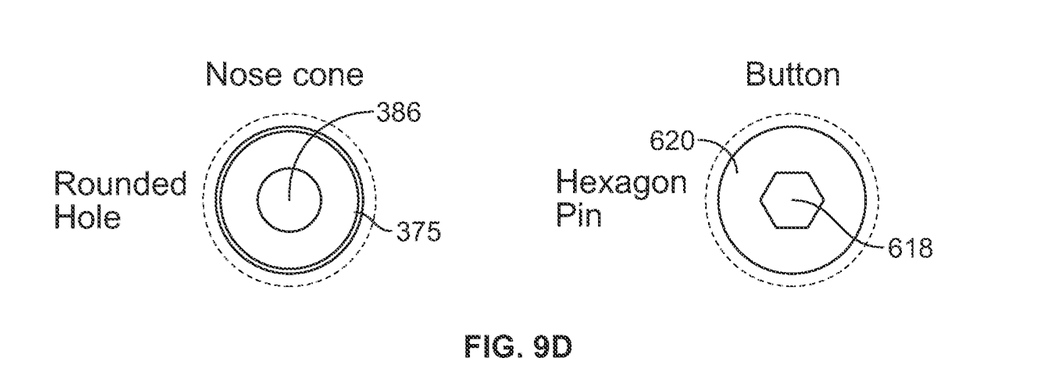
Figure 9E:
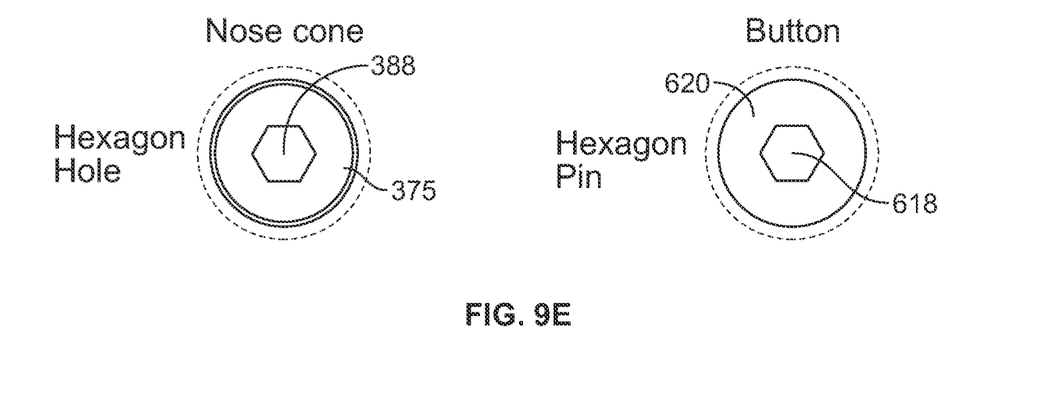

FIG. 9A indicates a tri-lobe mounting guide 380 in the extended neck 375 guide which receives a generally round or ovoid pin 612 extended from the body 620. FIG. 9B indicates a ribbed tri-lobe mounting guide 382 in the extended neck 375 guide which receives a generally tri-lobe pin 614 extended from the body 620. FIG. 9C indicates a square mounting guide 384 in the extended neck 375 guide which receives a generally square pin 616 extended from the body 620. FIG. 9D indicates a rounded mounting guide 386 in the extended neck 375 guide which receives a generally geometric (hexagon in this instance) pin 618 extended from the body 620. Rib 383 is deformable upon insertion of pin 614. FIG. 9E indicates a generally geometric mounting guide 388 in the extended neck 375 guide which receives a generally geometric (hexagon in this instance) pin 618, pin 614 extended from the body 620. The pin and mounting guide cooperate in mounting via deformation fit, friction fit, adhesive fit, pressure fit and the like.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description.

They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A method of setting a torque limiting limit; the method comprising:
   providing at least two swappable torque limiting fixtures (STLF), each of which is elongated and has a flange on one side, a body, and a mounting pin on the other side, wherein when mounted the STU: sets a predetermined torque;
   selecting one of the at least two STFLs;
   inserting the mounting pin through a coil spring;
   inserting a dutch with a first gear on one side at least partially over the coil spring;
   inserting the first gear, through a first section of a hollow base and into engagement an annular wall separating the first section of the hollow base from a second section, a channel passing through the annular wall between the first section and the second section of the hollow base, with the clutch further comprising a shoulder surrounding the first gear and the shoulder resting on a first surface of the annular wall of the hollow base; inserting an elongated nose with a tool mounting guide and a bearing surface surrounding a second gear and a pin mounting guide formed in the center of the second gear into the second section of the hollow base, with the bearing surface resting on a second surface of the annular wall of the hollow base, wherein the second surface of the annular wall is opposite of the first surface of the annular wall; and,
   mounting the mounting pin into the pin mounting guide;
   wherein the mounting pin and the pin mounting guide comprise different materials with one material being more deformable than the other, and wherein the more deformable of the mounting pin and the pin mounting guide deforms during the mounting of the mounting pin into the pin mounting guide.

2. The method of claim 1, the method further comprising placing an identifier on the back side of the flange.

3. The method of claim 2, the method further comprising fitting a cap into the first section of the hollow base and having a window through the back of the cap.

4. A method for forming a torque limiting device comprising:
   providing a kit with at least two swappable torque limiting fixtures (STLF), each of which is elongated and has a flange on one side a body of a preselected length and a mounting pin on the other side, wherein when mounted each STLF sets a different predetermined torque;
   providing at least one hollow base with a first and a second section separated by an internal annular wall having a channel passing there through;

selecting a STLF with a specific predetermined torque from the STLFs provided;

inserting the mounting pin of the selected STLF through a coil spring;

inserting a clutch with a first gear on one side at least partially over the coil spring;

inserting the first gear, through the first section of the hollow base and into the channel in the annular wall, the channel passing through the annular wall between the first section and the second section of the hollow base, with the clutch further comprising a shoulder surrounding the first gear and the shoulder resting on a first surface of the annular wall of the hollow base;

inserting an elongated nose with a tool mounting guide and a bearing surface surrounding a second gear and a pin mounting guide formed in the center of the second gear into the second section of the hollow base, with the bearing surface resting on a second surface of the annular wall of the hollow base, wherein the second surface of the annular wall is opposite of the first surface of the annular wall; and, mounting the mounting pin into the pin mounting guide; wherein the mounting pin and the pin mounting guide comprise different materials with one material being more deformable than the other, and wherein the more deformable of the mounting pin and the pin mounting guide deforms during the mounting of the mounting pin into the pin mounting guide.

5. The method of claim 4, the method further comprising placing an identifier on the back side of the flange.

6. The method of claim 5, the method further comprising fitting a cap into the first section of the hollow base and having a window through the back of the cap.

7. The method of claim 1, wherein the mounting pin comprises a material which is more deformable than the material of the pin mounting guide and the mounting pin deforms to fit into the pin mounting guide.

8. The method of claim 1, wherein the mounting pin comprises a material which is less deformable than the material of the pin mounting guide and the pin mounting guide deforms to accommodate the mounting pin.

9. The method of claim 8, wherein:
the pin mounting guide comprises a ribbed tri-lobe mounting guide having a deformable rib therein;
the mounting pin comprises a tri-lobe pin; and
the deformable rib is deformed upon mounting of the mounting pin into the pin mounting guide.

10. The method of claim 4, wherein the mounting pin comprises a material which is more deformable than the material of the pin mounting guide and the mounting pin deforms to fit into the pin mounting guide.

11. The method of claim 4, wherein the mounting pin comprises a material which is less deformable than the material of the pin mounting guide and the pin mounting guide deforms to accommodate the mounting pin.

12. The method of claim 11, wherein:
the pin mounting guide comprises a ribbed tri-lobe mounting guide having a deformable rib therein;
the mounting pin comprises a tri-lobe pin; and
the deformable rib is deformed upon mounting of the mounting pin into the pin mounting guide.

* * * * *